(12) United States Patent
Valyunin et al.

(10) Patent No.: US 6,884,263 B2
(45) Date of Patent: Apr. 26, 2005

(54) ACCOMMODATIVE INTRAOCULAR LENS

(75) Inventors: Igor Valyunin, Laguna Niguel, CA (US); Stephen Q. Zhou, Irvine, CA (US)

(73) Assignee: Medennium, Inc., Irvine, CA (US)

( * ) Notice: Subject to any disclaimer, the term of this patent is extended or adjusted under 35 U.S.C. 154(b) by 89 days.

(21) Appl. No.: 10/188,677

(22) Filed: Jul. 2, 2002

(65) Prior Publication Data

US 2003/0018384 A1 Jan. 23, 2003

Related U.S. Application Data

(60) Provisional application No. 60/306,031, filed on Jul. 17, 2001.

(51) Int. Cl.[7] .................................................. A61F 2/16
(52) U.S. Cl. ..................................... 623/6.37; 623/6.39
(58) Field of Search .............................. 623/6.16, 6.19, 623/6.22, 6.24, 6.27–6.29, 6.34–6.35, 6.38, 6.39, 6.43, 6.46, 6.47

(56) References Cited

U.S. PATENT DOCUMENTS

| | | | | |
|---|---|---|---|---|
| 4,950,290 A | * | 8/1990 | Kamerling | .................. 623/6.42 |
| 5,275,623 A | * | 1/1994 | Sarfarazi | .................... 623/6.13 |
| 5,326,347 A | | 7/1994 | Cumming | |
| 5,476,514 A | | 12/1995 | Cumming | |
| 5,496,366 A | | 3/1996 | Cumming | |
| 5,674,282 A | | 10/1997 | Cumming | |
| 6,013,101 A | | 1/2000 | Israel | |
| 6,136,026 A | | 10/2000 | Israel | |
| 6,176,878 B1 | | 1/2001 | Gwon et al. | |
| 6,197,059 B1 | | 3/2001 | Cumming | |
| 6,231,603 B1 | | 5/2001 | Lang et al. | |
| 6,454,801 B1 | * | 9/2002 | Portney | ...................... 623/6.34 |
| 6,488,708 B1 | * | 12/2002 | Sarfarazi | .................... 623/6.34 |
| 6,506,212 B1 | * | 1/2003 | Zhou et al. | ................. 623/6.38 |
| 6,558,420 B1 | * | 5/2003 | Green | ........................ 623/6.34 |
| 6,599,317 B1 | * | 7/2003 | Weinschenk, III et al. | 623/6.34 |
| 2002/0107568 A1 | * | 8/2002 | Zadno-Azizi et al. | ...... 623/6.37 |

FOREIGN PATENT DOCUMENTS

EP    WO 92/10980    *    7/1992    ................. 623/6.29

OTHER PUBLICATIONS

Koretz and Handelman, "How the Human Eye Focuses," Scientific American, Jul. 1988, pp 64–71.

* cited by examiner

Primary Examiner—Suzette J Jackson
(74) Attorney, Agent, or Firm—Frost Brown Todd LLC

(57) ABSTRACT

An accommodative intraocular lens is disclosed. The lens provides multiple focuses as the result of a bi-directional shift along the eye's optical axis, and also minimizes or prevents posterior chamber opacification. The lens includes a first component which consists of an optical body and a haptic body, a second component which is structurally adapted to maintain substantial contact with the posterior surface of the capsular bag of the eye (when implanted in the eye), and a transition zone connecting the first and second components. The method of implanting the lens in the eye and the method of making the lens are also disclosed.

11 Claims, 10 Drawing Sheets

(a)

(b)

ACCOMMODATIVE INTRAOCULAR LENS

CROSS-REFERENCE TO RELATED APPLICATION

This application claims priority from U.S. Provisional Patent Application No. 60/306,031, filed Jul. 17, 2001.

TECHNICAL FIELD

The present invention relates to accommodative intraocular lenses used to replace the aged human natural lens to provide multiple focuses by bi-directional shift of the lens optics along the eye's optical axis. The design of the present invention also prevents posterior chamber opacification, a condition normally associated with the removal of the natural human lens, which may lead to secondary cataract formation.

BACKGROUND OF THE INVENTION

In order for the human eye to have clear vision of objects at different distances, the effective focal length of the eye must be adjusted to keep the image of the object focused as sharply as possible on the retina. This change in effective focal length is known as accommodation and is accomplished in the eye by varying the shape of the crystalline lens. Generally, in the unaccommodated emmetropic eye, the curvature of the lens is such that distant objects are sharply imaged on the retina. In the unaccommodated eye, near images are not focused sharply on the retina because the focal points of their images lie behind the retinal surface. In order to visualize a near object clearly, the curvature of the crystalline lens must be increased, thereby increasing its refractive power and causing the focal point of the near object to fall on the retina.

The change in shape of the crystalline lens is accomplished by the action of certain muscles and structures within the eyeball or globe of the eye. The lens is located in the forward part of the eye, immediately behind the pupil. It has the shape of a biconvex optical lens, i.e., it has a generally circular cross-section of two-convex-refracting surfaces, and is located generally on the optical axis of the eye, i.e., a straight line drawn from the center of the cornea to the macula in the retina at the posterior portion of the globe. Generally, the curvature of the posterior surface of the lens, i.e., the surface adjacent to the vitreous body, is somewhat greater than that of the anterior surface. The lens is closely surrounded by a membranous capsule that serves as an intermediate structure in the support and actuation of the lens. The lens and its capsule are suspended on the optical axis behind the pupil by a circular assembly of many radially-directed collagenous fibers, the zonules, which are attached at their inner ends to the lens capsule and at their outer ends to the ciliary body, a muscular ring of tissue located just within the outer supporting structure of the eye, the sclera. The ciliary body is relaxed in the unaccommodated eye and therefore assumes its largest diameter. According to the classical theory of accommodation, the relatively large diameter of the ciliary body in this condition causes a tension on the zonules which in turn pull radially outward on the lens capsule, causing the equatorial diameter of the lens to increase slightly, and decreasing the anterior-posterior dimension of the lens at the optical axis. Thus, the tension on the lens capsule causes the lens to assume a flattened state wherein the curvature of the anterior surface, and to some extent of the posterior surface, is less than it would be in the absence of the tension. In this state, the refractive power of the lens is relatively low and the eye is focused for clear vision of distant objects, i.e., the unaccommodated state.

In an accommodative state, however, the eye is intended to be focused on a near object, the muscles of the ciliary body contract. This contraction causes the ciliary body to move forward and inward, thereby relaxing the outward pull of the zonules on the equator of the lens capsule. This reduced zonular tension allows the elastic capsule of the lens to contract causing an increase in the anterior-posterior diameter of the lens (i.e., the lens becomes more spherical) resulting in an increase in the optical power of the lens. Because of topographical differences in the thickness of the lens capsule, the central anterior radius of curvature decreases more than the central posterior radius of curvature. This is the accommodated condition of the eye wherein the image of near objects falls sharply on the retina. See Koretz, et al., Scientific American, July, 1988, pages 64–71.

In a simplified model, zonules work like a spring with one end attached to the elastic lens and the other end attached to ciliary muscles. In an unaccommodated state, the spring is pulled taut by the ciliary muscles to force the elastic lens to become thin; in an accommodated state, the spring relaxes to relieve the elastic lens so that it becomes thick (see FIGS. 1a and 1b). In a young and healthy eye, the elastic lens can become thin (low diopter) or thick (high diopter) with about 3 diopters difference. Starting at age mid-forty, a typical eye begins to gradually lose its near distance vision (presbyopia). There are multiple reasons for loss of accommodation. One of them is that the human lens becomes too hard to change back and forth from a thin lens to a thick lens.

The common approach for addressing the problem of the loss of accommodation is to wear reading glasses. However, various attempts have been made to solve presbyopia by implanting an accommodating IOL. A number of U.S. Patents disclose various means for moving the optical body of an IOL along the optical axis anteriorly or posteriorly so that optical power of the IOL can be adjusted to provide either near vision or far vision. For example, Cumming, in his U.S. Pat. Nos. 6,197,059 (issued Mar. 6, 2001) and 5,476,514 (issued Dec. 19, 1995), discloses an accommodating intraocular lens design similar to a plate IOL except that there is a guiding hinge on each side of the haptics (see FIG. 2). The guiding hinge is intended to facilitate the lens in vaulting anteriorly for near vision or posteriorly for distance vision. In other words, the change in lens focus power measured in diopter is achieved by a bi-directional shift of the IOL guided by the hinge, along the optical axis. The more the shifting distance toward the anterior chamber, the more the focus power for the lens. Gwon, in U.S. Pat. No. 6,176,878 (issued Jan. 23, 2001), discloses an accommodating lens design which is adapted to cooperate with the eye to move the optic body bi-directionally, that is anteriorly or posteriorly in the eye. Similarly, Israel, in U.S. Pat. No. 6,013,101 (issued Jan. 11, 2000), discloses another accommodating lens design with haptics in engagement with zonule movement to achieve a bi-directional shift of the lens along the optical axis. In summary, all of these prior art patents utilize various mechanisms to move the optical body of the IOL either anteriorly or posteriorly to achieve near vision, or far vision respectively.

Sarfarazi, in U.S. Pat. No. 5,275,623, issued Jan. 4, 1994, discloses an elliptical accommodating IOL with two optical bodies positioned in the anterior surface and posterior surface respectively. The lens is a closed cell containing fluids. The accommodation is achieved by adjusting the distance between the two optical bodies of the elliptical IOL.

Although accommodating IOL's are known, there is one common complication associated with the IOL implantation:

that is posterior chamber opacification (PCO), where cells migrate from equatorial peripheries towards the center of the capsular bag. These cells block incoming light from reaching the retina. Consequently, PCO will cause gradual vision loss, and in some cases complete vision loss, if untreated. This cell migration after cataract surgery is also known as secondary cataract formation.

None of the prior art patents on accommodative lenses includes a feature designed for addressing the PCO problem. In fact, some of the designs disclosed in the prior art may invite the epithelial cells in-growth. For example, FIG. 2 is derived from U.S. Pat. No. 6,197,059, where the IOL is in the backward and forward positions, respectively. The gap between the IOL and posterior surface of the capsular bag in the forward position may invite the growth of epithelial cells so that eventually epithelial cells will occupy any existing space in the capsular bag. Consequently, that structure could lead to secondary cataract formation. Furthermore, the epithelial cell's in-growth into the gap may hinder and eventually prevent the IOL from shifting along the optical axis, thus resulting in a loss in accommodation once again.

It has been estimated that about one-third of the patients who undergo cataract surgery with IOL implantation will eventually develop PCO or secondary cataract formation. The common procedure for treating PCO is using a Yag laser. The laser beam burns cells situated in its pathway to allow images to reach and focus on the retina again so patients regain their vision. This laser treatment is not only a costly procedure but also involves significant risks for the patient. For example, if the laser beam is focused on any part of the eye tissue by mistake, it will cause unnecessary permanent tissue damage or possibly even permanent vision loss.

Accordingly, there is a great need to provide an accommodating lens which can avoid or reduce the possibility of forming a secondary cataract. The present invention discloses a family of accommodating lenses designed to avoid secondary cataract formation while providing accommodating capabilities.

SUMMARY OF THE INVENTION

The present invention provides an accommodative intraocular lens for replacing the aged human natural lens. The lens provides multiple focuses utilizing a bi-directional shift of the lens optics along the eye's optical axis. The lenses of the present invention also prevent posterior chamber opacification, a condition normally associated with the removal of the natural human lens which may lead to secondary cataract formation. These intraocular lenses comprise:

i. a first component which consists of an optical body and a haptic body adjacent and attached to said optical body;

ii. a second component, located posterior to said first component, which is structurally adapted to maintain substantial contact with the posterior surface of the capsular bag when implanted in the eye; and iii. a transition zone which smoothly connects the first and the second components;

the lens being configured so as to allow the first component to move forward and back relative to the second component, along the optical axis of the optical body.

The accommodative lens structures may optimally include additional optional features, such as guiding grooves for assisting the bi-directional shift of the first component of the lens.

The present invention also encompasses the method of implanting these accommodative lenses in the eye.

Lastly, because of the complexity of the lens structure in the present invention, a novel method of molding such lenses in a three-piece mold is also disclosed.

DETAILED DESCRIPTION OF THE INVENTION

The present invention provides an accommodating lens for patients whose natural lens has been removed. It also provides an accommodating lens which can avoid secondary cataract formation. These and other additional objects are achieved by providing an accommodating lens which has two main components. The first component is for providing the optical function as the lens and the second component is for preventing PCO. Additional optional lens structure features include a guiding function which directs the optical body of the lens in its bi-directional movement, i.e., towards the anterior or posterior chambers along the eye's optical axis, corresponding to the contraction or relaxation of the ciliary muscle via the zonules.

Figure 3:
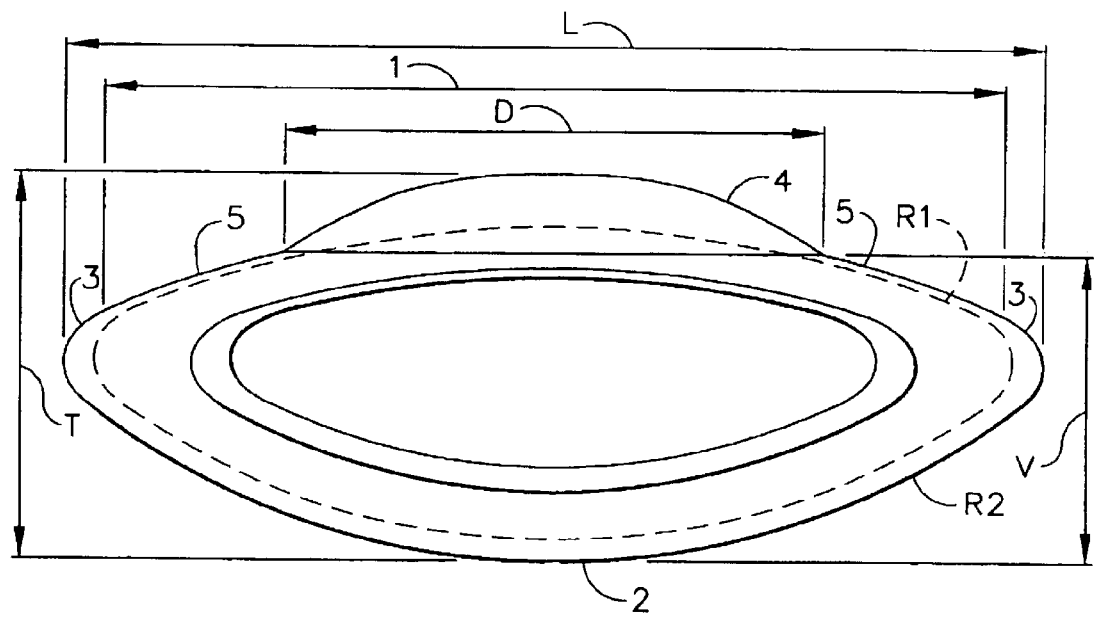
FIG. 3 is a schematic cutaway view of one embodiment of the present invention.
Figure 4:
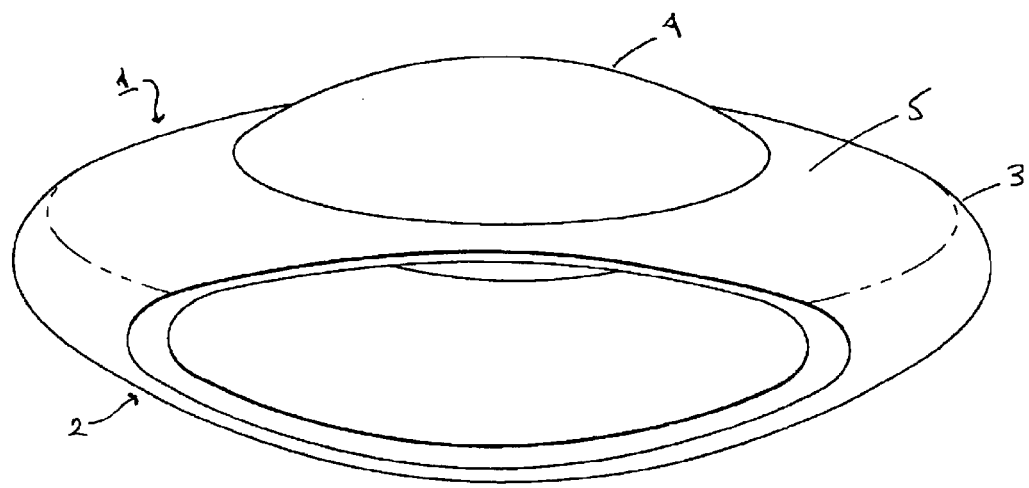
FIG. 4 is the isometric view of the lens of FIG. 3.
Figure 6:
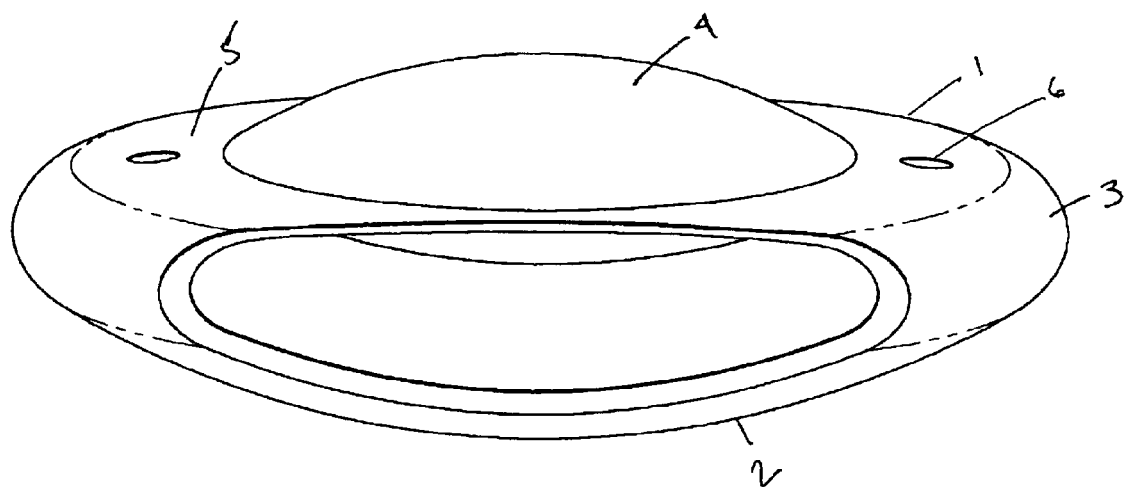
FIG. 6 is an isometric view of an embodiment of the present invention similar to FIG. 4 except that there are fenestration holes in the haptic body.
Figure 7:
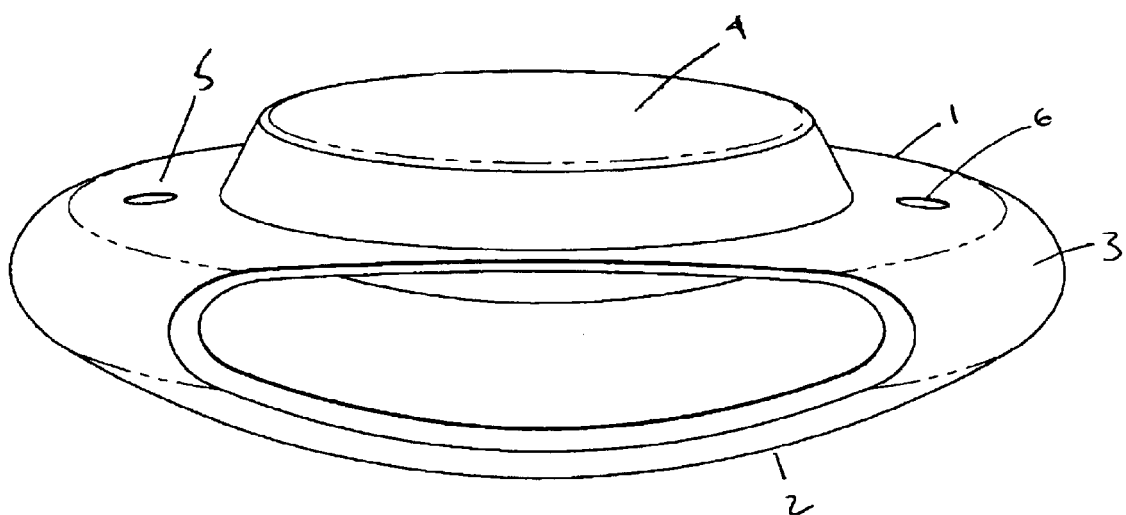
FIG. 7 is an isometric view of an embodiment of the present invention similar to FIG. 6 except the optical body in FIG. 7 is a negative lens while FIG. 6 has a positive optical body.

One embodiment in accordance with the present invention is an accommodating lens design as illustrated in FIG. 3 and its isometric view in FIG. 4. FIG. 6 is an isometric view of an embodiment of the present invention similar to that shown in FIG. 4, except there are fenestration holes (6) in the haptic body. FIG. 7 is an isometric view of an embodiment of the present invention similar to FIG. 6 except that the optical body in FIG. 7 is a negative lens while the optical body in FIG. 6 is a positive lens. The lens has two components 1 and 2 as well as a transition zone (3). Component 1 is the anterior portion of the lens containing an optical body (4) with an optical diameter in the range of from about 4 to about 7 mm and a haptic body(5). The haptic bodies (5) extend outward from opposite edges of the optical body (4). The optical body can be designed to be a positive or negative lens with any optical configurations, such as biconvex, biconcave, plano-convex, or plano-concave. Component 1 also has a first radius of curvature (R1 in FIG. 3) similar to that of a human natural lens usually in the range of from about 8 to about 13 mm, preferably from about 9 to about 11 mm. The main function of component 1 is that its optical powers measured in diopters can be changed by shifting the optical element along the optical axis towards or away from the posterior chamber. Typically, the lens' overall central thickness (T in FIG. 3) is in the range of about 2 to about 5 mm, preferably from about 3 to about 4 mm. The overall length (L in FIG. 3) of the lens is in the range of from about 8 to about 13 mm, preferably from about 8 to about 11 mm.

Component 2 is the posterior portion of the lens with the second radius of curvature (R2 in FIG. 3) which approximately matches with that of the human capsule, such as from about 5 to about 9 mm, preferably from about 6 to about 7.5 mm. In this way, component 2 maintains a tight contact with the posterior bag tissue. The main purpose for component 2 is to provide a means to prevent epithelial cells from growing into the central lens area so that the PCO can be avoided. Since this second component is located posterior to the optical body, it must allow light to pass through it (for example, by being optically transparent or by having a cut-out section along the line of the optical axis of the first component). The transition zone (3) connects component 1 with component 2 and blends the two radii of curvature in a smooth way. Thus, the transition zone begins at the end of the haptics and continues until the beginning of the radius of curvature of component 2 is reached. The main function of the transition zone is to assist the accommodative lens to change focus by axial shift (forward and back) of the optic body.

Figure 5A:
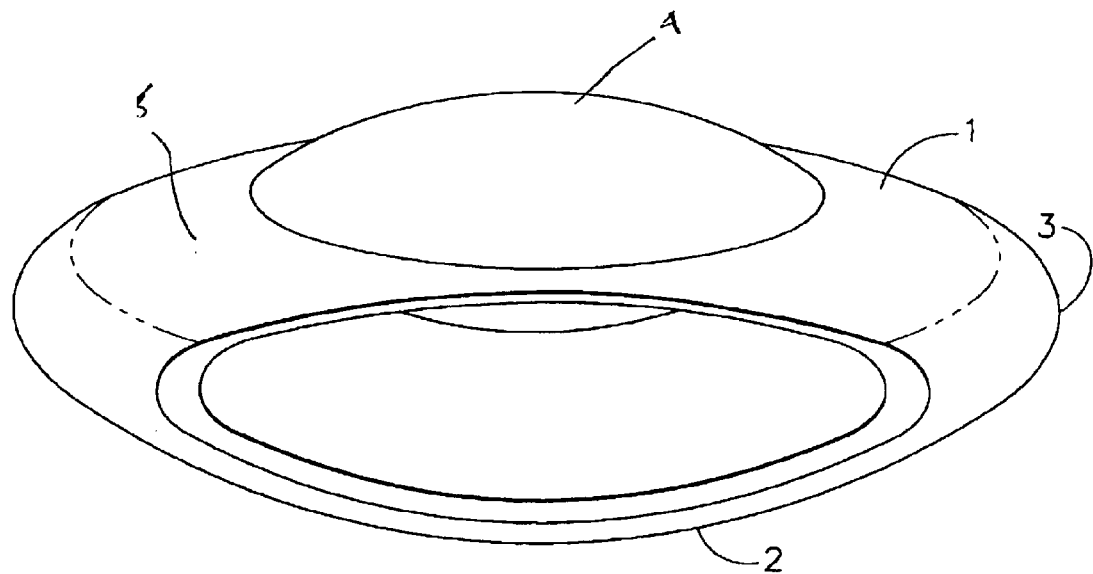
FIG. 5(a) and FIG. 5(b) are isometric views of a lens of the present invention in its accommodated state and unaccommodated state respectively.
Figure 5B:
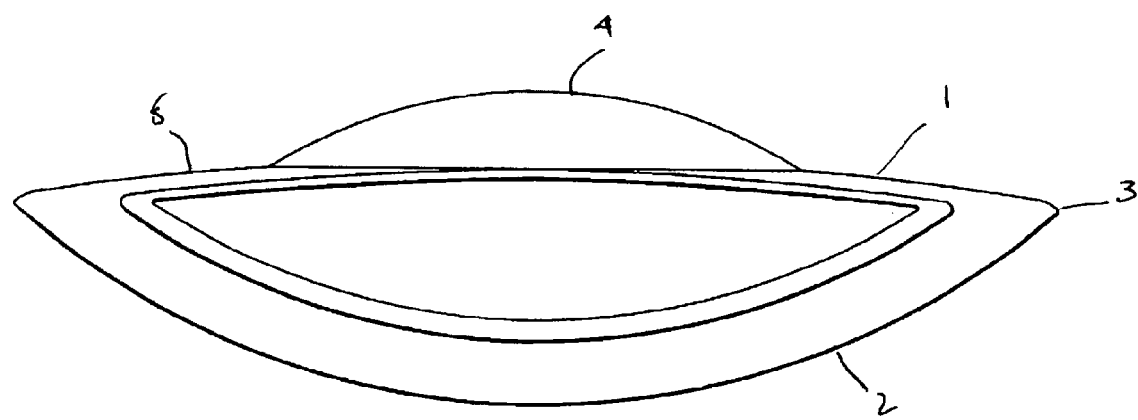
Figure 5C:
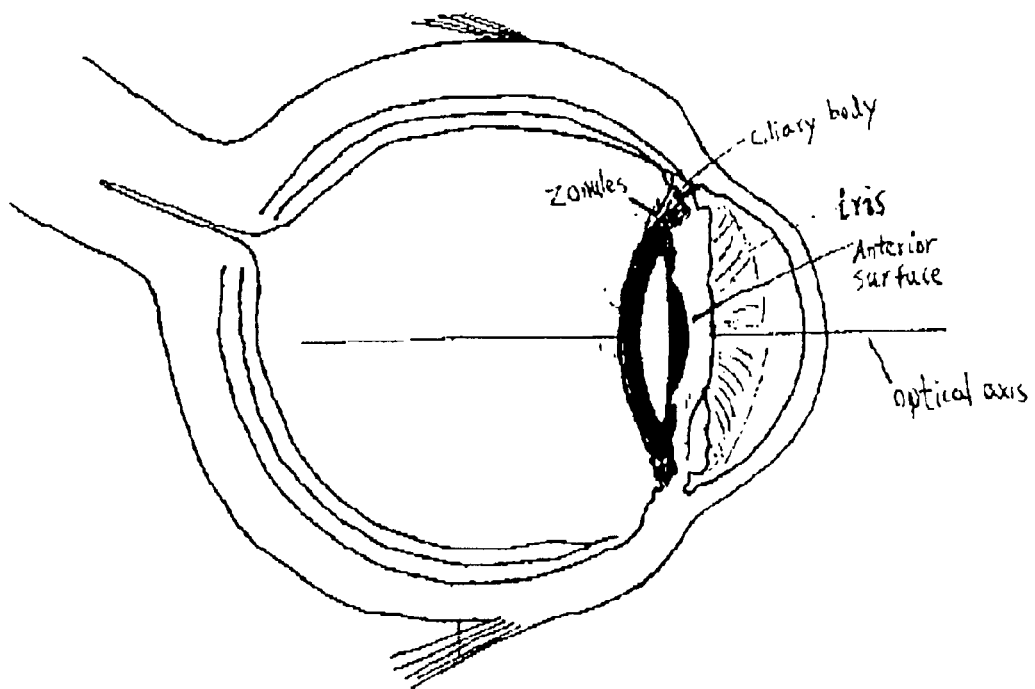
FIGS. 5(c) and 5(d) are schematic views showing placement of the lens in the eye.
Figure 5D:
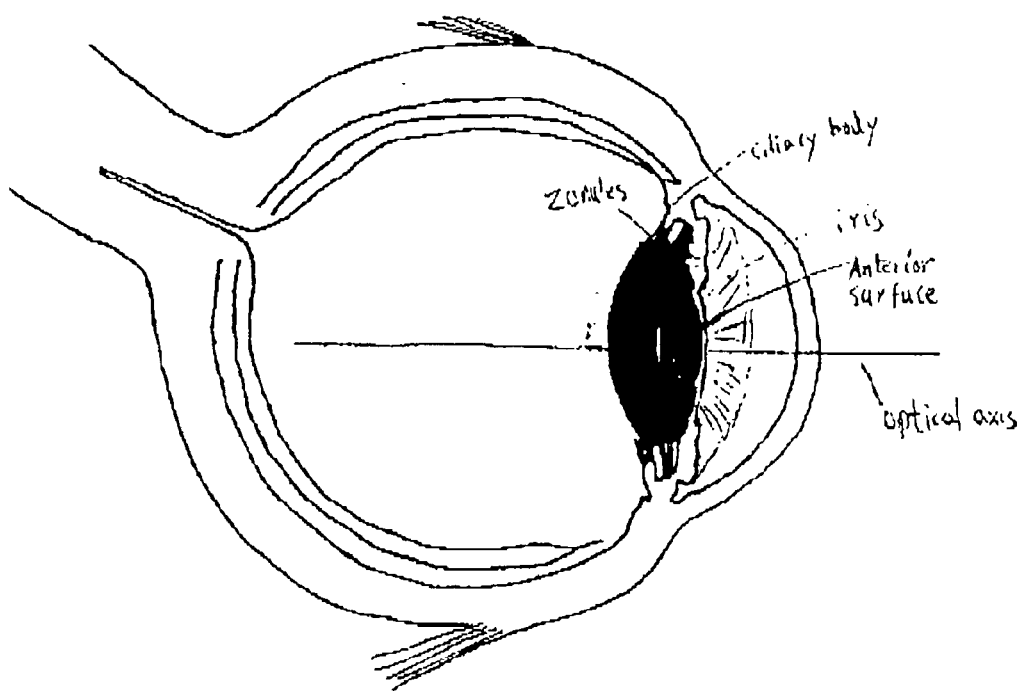

This axial shift of the optical body of the IOL can be achieved as a result of its material's shape memory properties or its structural configurations, or both. For example, an accommodative IOL can be made from elastomeric polymers having appropriate shape memory properties. Such elastomeric polymers are known in the art and include, but are not limited to, silicones, acrylic polymers, and hydrogels. The materials used to make the lenses of the present invention are optically clear and of sufficient purity and biocompatibility to permit placement in the eye. Structurally, the IOL comprises component 1 (optical body+ haptics), component 2 (the posterior portion of the lens), and a transition zone. Component 1 is the optical body with a first radius of curvature and component 2 has a second radius of curvature, connected by a transitional area which blends components 1 and 2 in a smooth way. Generally, the IOL is made in its accommodated state, with the first radius (R1) being larger than the second radius (R2). When implanted in the eye (see FIGS. 5(c) and (d)), the accommodating lens maintains its initial shape, i.e., when the ciliary muscle relaxes. When ciliary muscle contracts, it tightens up the zonules. This stretches the accommodative IOL so that component 1, i.e., the optical lens, will move along the optical axis toward the posterior chamber. As a result, the optical power of the lens is reduced due to the shift of the lens along the optical axis, thereby providing far distance vision (see FIGS. 5(b) and 5(d)). When the zonule stretching force is absent, the accommodative IOL returns to its initial accommodative lens state due to its material shape memory or elasticity (see FIGS. 5(a) and 5(c)). Note that in FIGS. 5(c) and 5(d), when the lens is implanted in the eye, component 2 is in contact with the posterior surface of the capsular bag. This contact prevents or minimizes secondary cataract formation, and helps transmit ciliary muscle force to the lens.

Figure 12:
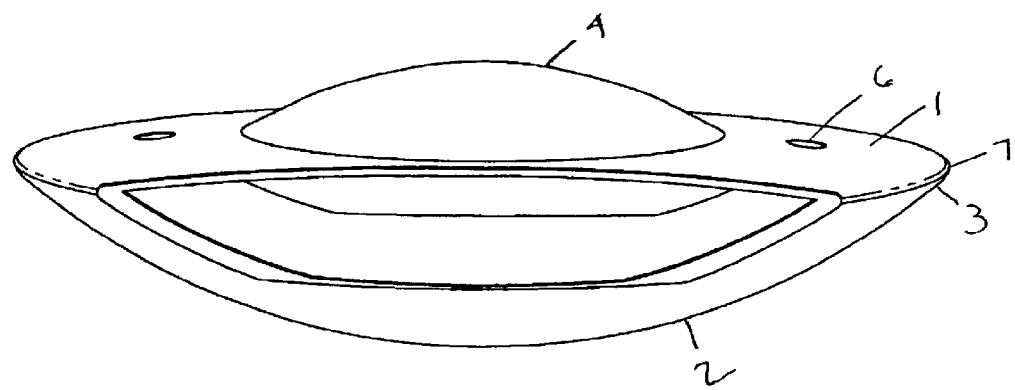
FIGS. 12 and 13 are isometric views of two additional embodiments of the present invention.
Figure 13:
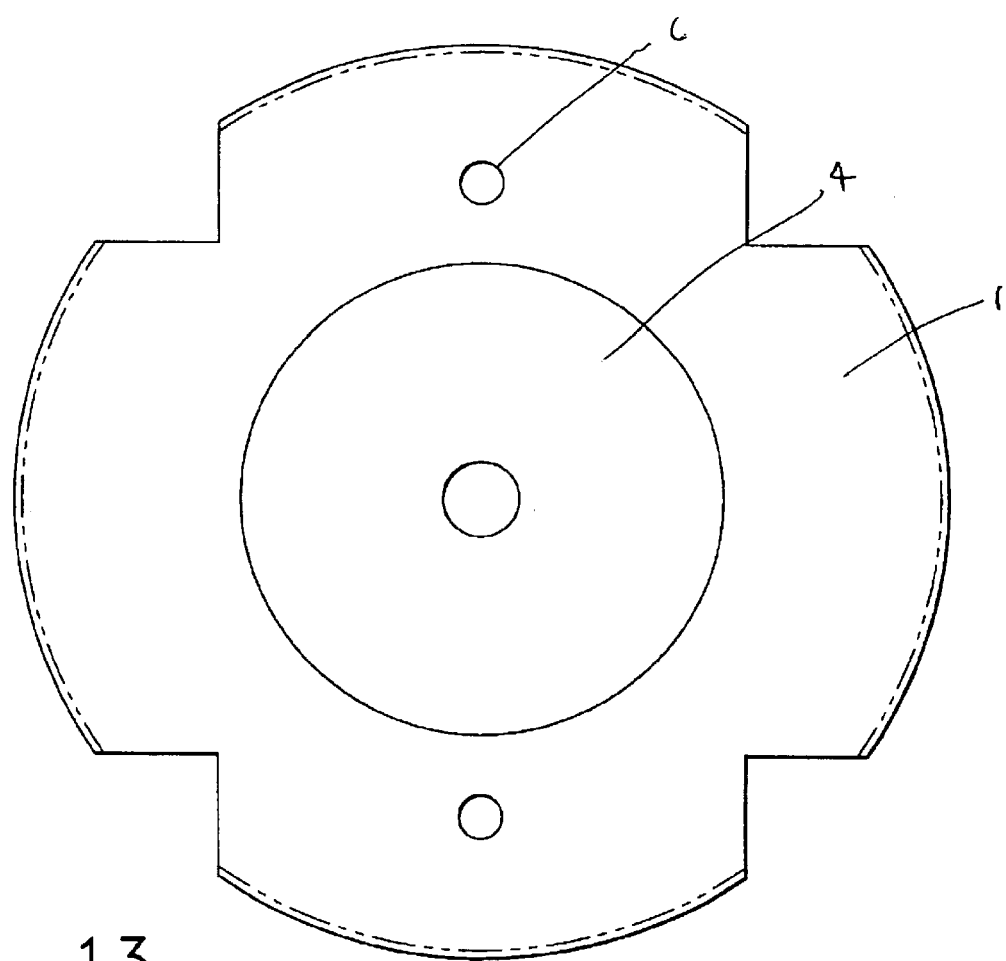

Additional design features include the selection of different thicknesses for the first component and second component. For example, when the second component has a larger thickness than the haptics of the first component, the second component has a stronger mechanical strength than the first component. In other words, the second component works as an arch to support the first component. When the zonules pull the accommodative lens, the arch will extend outwardly while still maintaining close contact with the posterior surface of the capsular bag. The first component will shift its position toward the posterior chamber, equivalent to a change from an accommodated state to an unaccommodated state (See FIG. 5). Approximately, a 1 mm axial shift is equivalent to a change of about 1–2 diopters in optical power. FIGS. 12 and 13 are isometric views of two additional embodiments of the present invention.

Figure 11:
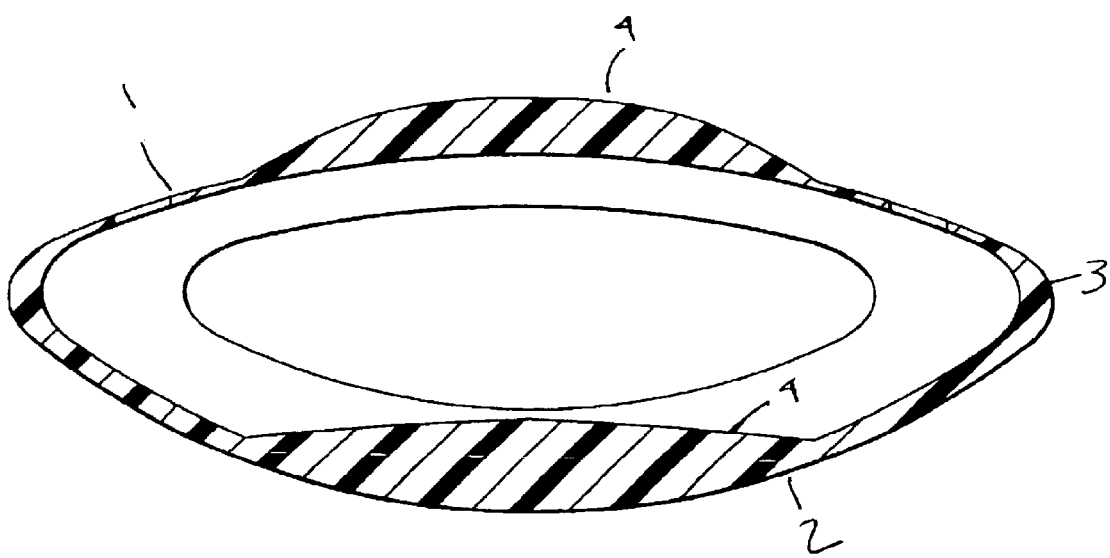
FIG. 11 is a perspective view of an embodiment of the present invention showing that part of the dioptic power may be provided by the second component of the lens.

It is also within the scope of the present invention that a portion of the diopter power can be provided by the second component. An example of this design is illustrated in FIG. 11. In any event, after implantation, component 2 must remain in a substantially close contact with the posterior surface of the capsular bag.

Figure 8:
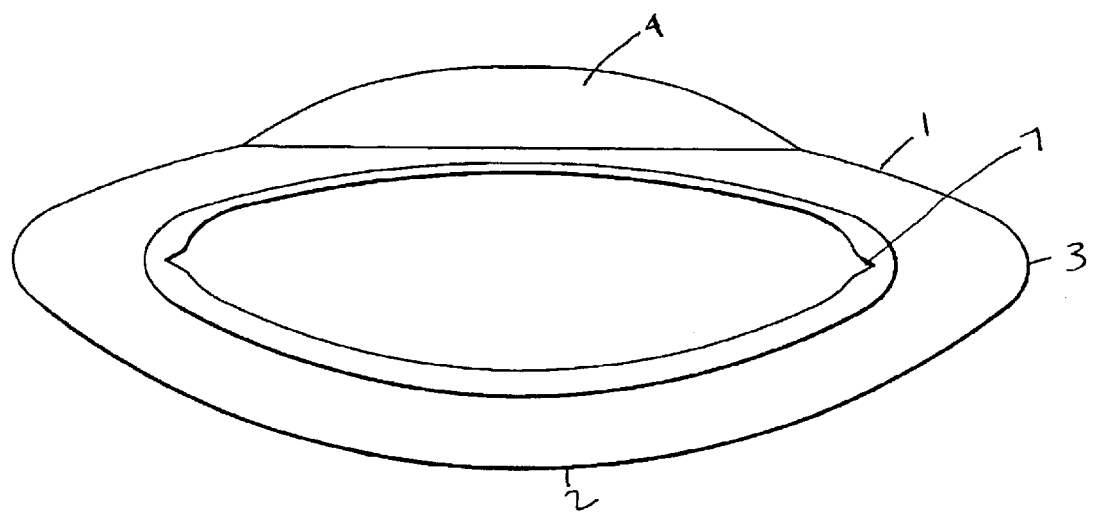
FIGS. 8 and 9 are isometric views of embodiments of the present invention including a groove in the transition zone.
Figure 9:
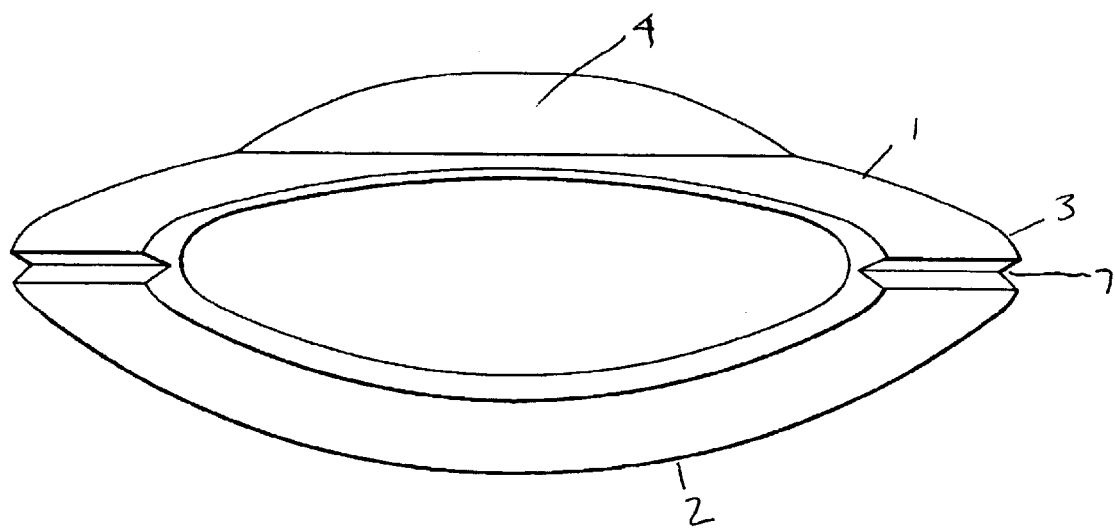
Figure 10:
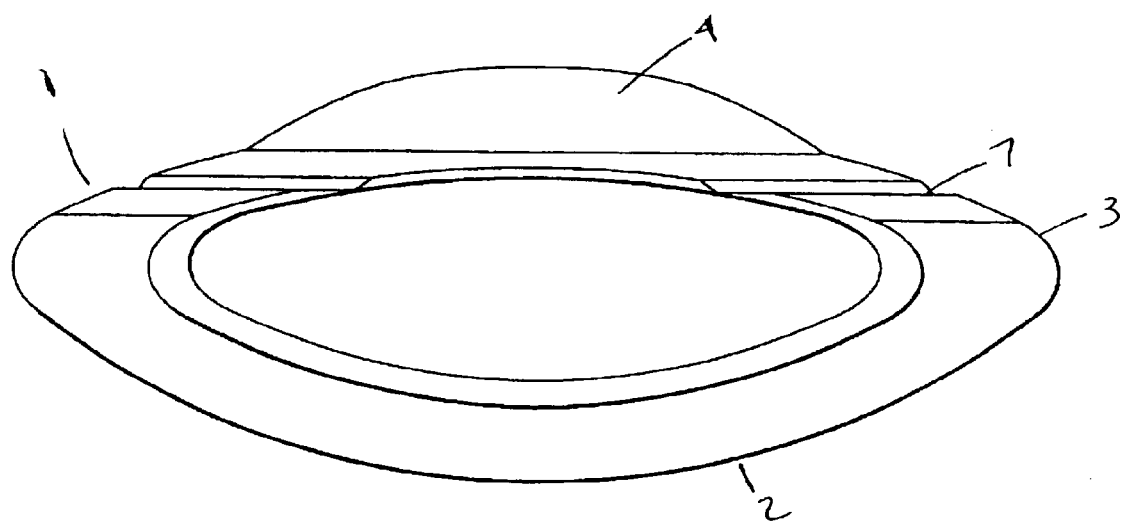
FIG. 10 is a perspective view of an embodiment of the present invention showing the groove in the haptic area.

The present invention may include guiding structures to help the lens shift in response to ciliary muscle movement. These guiding structures may, for example, be a groove (7) in the transition zone, such as illustrated in FIGS. 8, 9, or in the haptic body of component 1, as shown in FIG. 10. In a non-accommodative state, the zonules are tightened up. This flattens the IOL (particularly at the location of the guiding groove (7) and the optical body shifts toward the posterior chamber. This posterior shift is equivalent to the decrease of the optical power of the IOL. On the other hand, in an accommodative state, zonules are relaxed and the capsule recovers back to its un-stretched shape. This relaxation of zonules allows the first component of the accommodating lens to shift forward, i.e., move toward the anterior chamber, resuming its initial lens shape and optic power. This shape recovery is further assisted by a forward pushing force caused by a pressure increase due to the vitreous outflow from the posterior chamber to the interior chamber. This vault toward the anterior chamber is equivalent to an increase in the IOL's optical power, thereby, providing an improvement in near distance vision.

It is well known that when an intraocular lens is implanted in place of the natural lens, whether a cataract lens or a clear lens, there is always a possibility for PCO. The lens of the present invention minimizes or prevents PCO by always maintaining close contact with the capsular bag. This leaves no space for epithelial cells to grow into. To solve this PCO problem, the present invention provides a novel lens design which includes a second component having a radius of curvature similar to that of a human natural lens in the range of from about 5 to about 9 mm, preferably from about 6 to about 7.5 mm. This way, the second component usually maintains a close contact with the posterior surface of the capsular bag, preventing endothelial cells from growing into the space in between the implant and the capsular bag.

EXAMPLE—MOLDING OF THE ACCOMMODATIVE LENS

Figure 1:
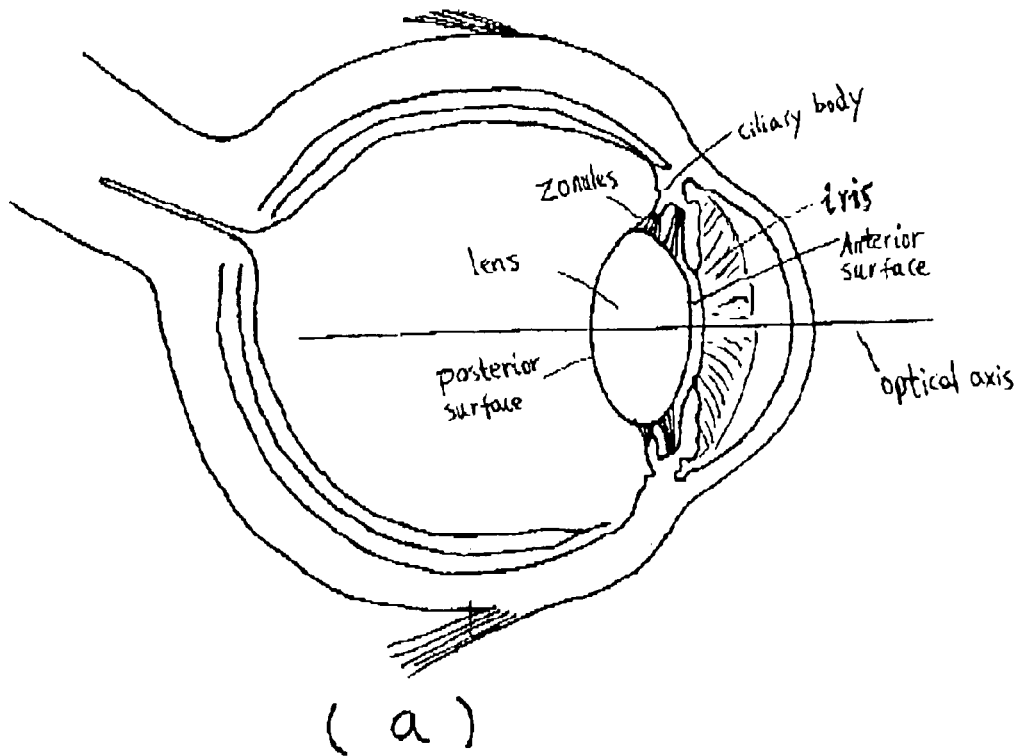
FIG. 1(a) is a schematic cutaway view of an eye in its unaccommodated state and FIG. 1(b) is a schematic cutaway view of an eye in its accommodated state.
Figure 1:
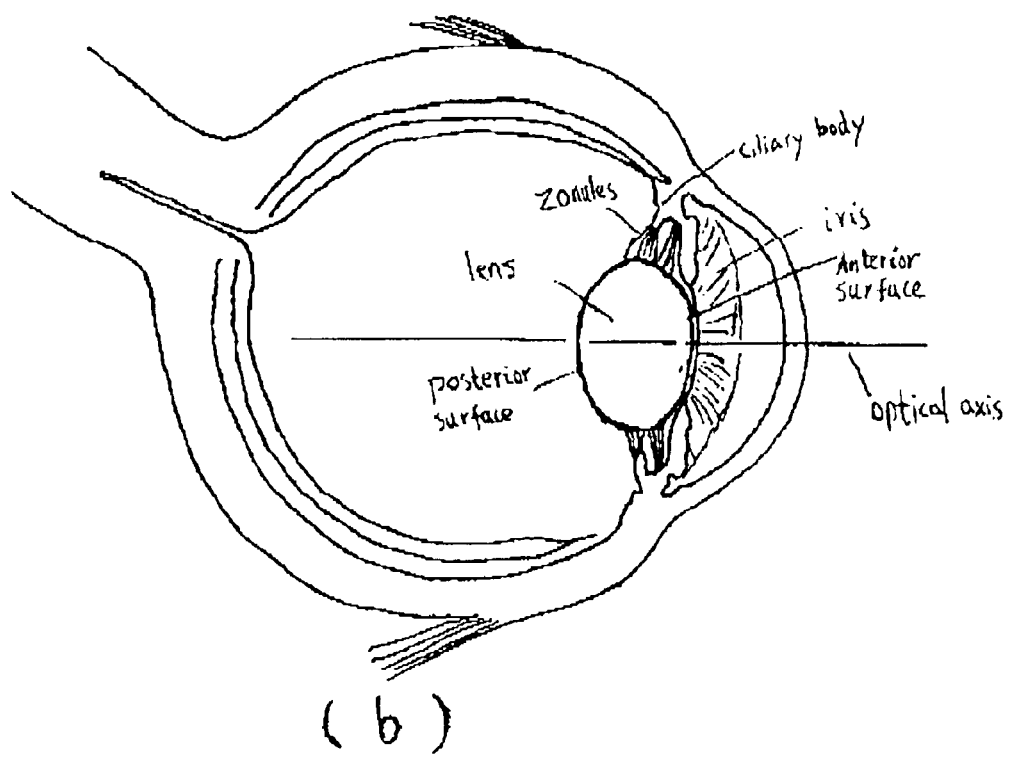
Figure 2:
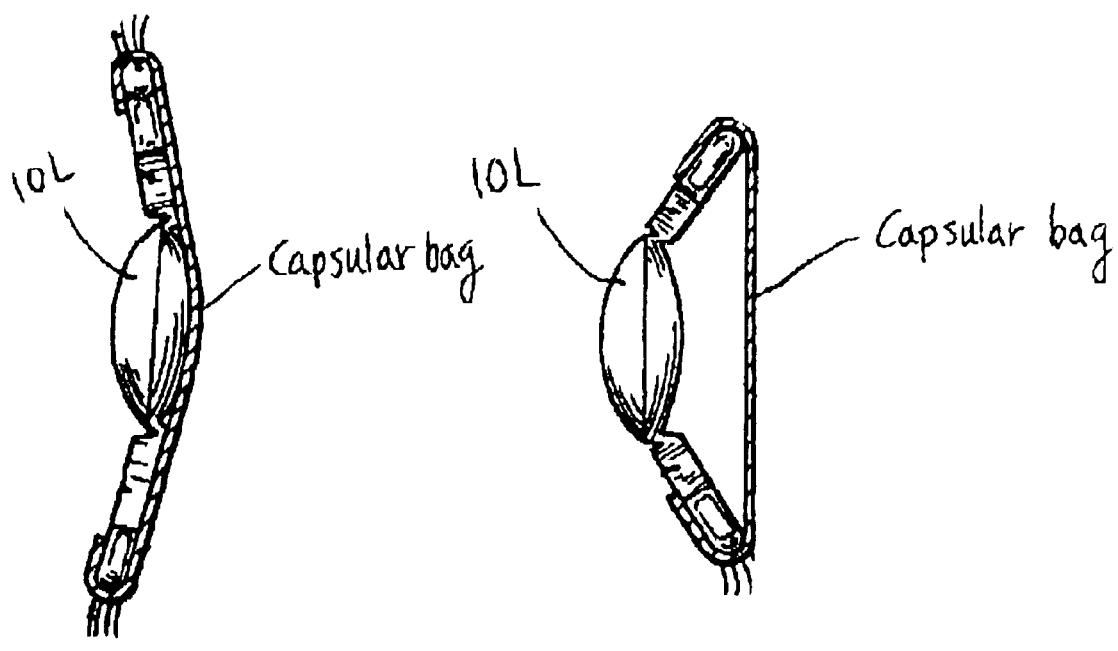
FIG. 2 is a side view of an example of an accommodative lens design from the prior art.
Figure 14:
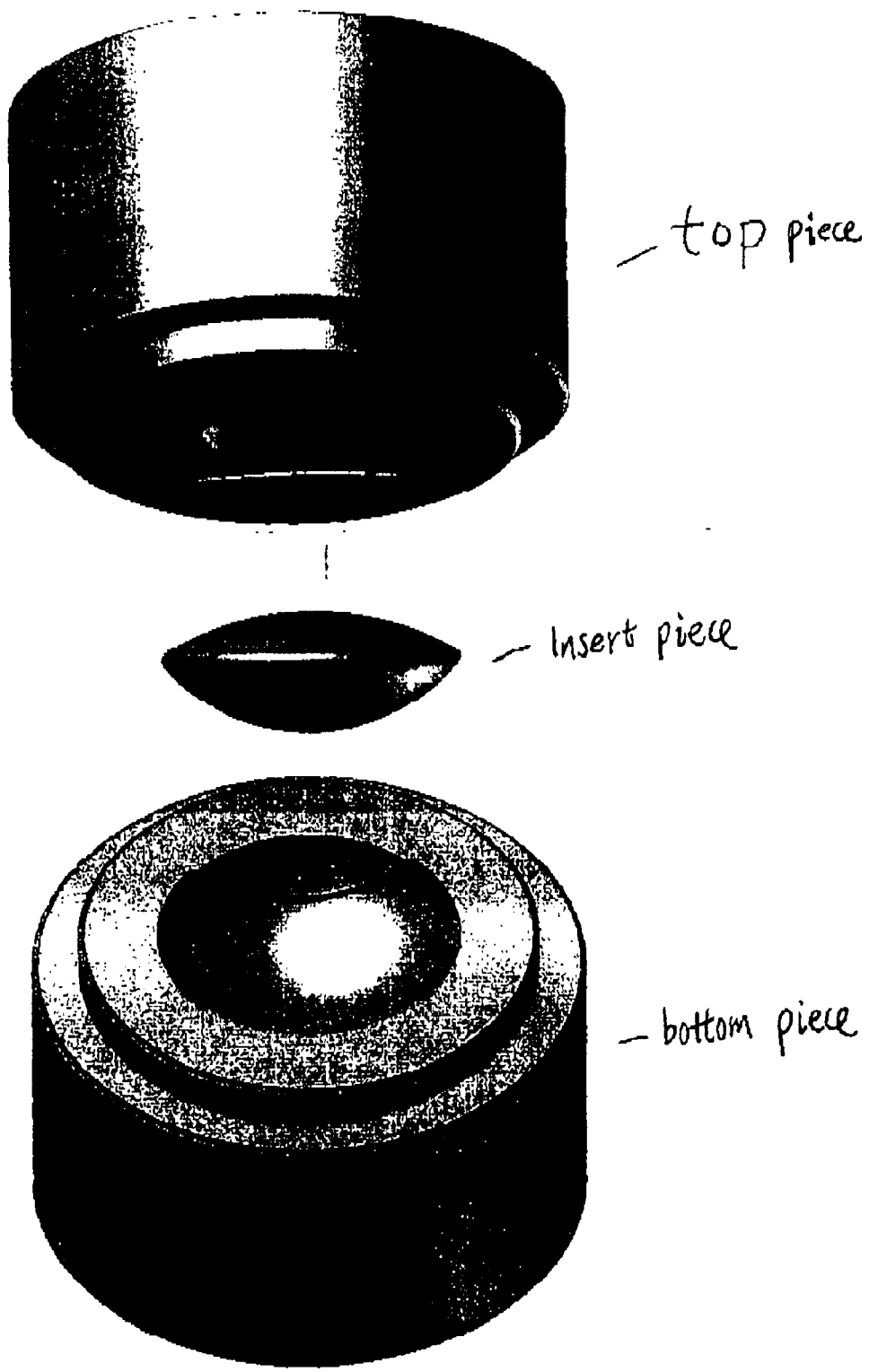
FIG. 14 shows the mold used for making the lenses of the present invention.

Intraocular lenses with designs similar to that shown in FIG. 2 have been successfully made as follows: In a three-piece (bottom piece, top piece, and the insert piece, see FIG. 14) stainless steel mold, was added an appropriate amount of medical grade silicone (NuSil Silicone Technology, MED 6820) onto the bottom piece. The insert piece was carefully placed on the center of the bottom piece followed by the top piece with appropriate lining. The closed mold was tightly clamped and placed in a pre-heated oven at a temperature in the range of 110–140° C. for about 30 to 60 minutes. When the mold cooled down to the room temperature, the top piece was removed. An aqueous lubricant, such as Healon (manufactured by Pharmacia), was used to wet the space between the insert piece and the intraocular lens. After the majority of the space was lubricated, the insert piece of the mold was pushed out while the lens remained on the bottom piece. The lens was carefully removed from the bottom piece.

What is claimed is:

1. An intraocular lens containing a single optical body, comprising:
   i. a first component which consists of said optical body and a haptic body adjacent and attached to said optical body;
   ii. a second component, located posterior to said first component, which is structurally adapted to maintain substantial contact with the posterior surface of the capsular bag when implanted in the eye;
   iii. a transition zone which smoothly connects the first component with the second component; the lens being configured so as to allow the first component to move forward and back relative to the second component, along the optical axis of the optical body; and
   iv. at least one groove acting as a guiding structure adapted to assist the optical body of said first component in shifting bi-directionally along said optical axis.

2. The intraocular lens of claim 1 wherein its overall diameter is from about 8 to about 13 mm.

3. The intraocular lens of claim 1 having a central lens thickness of from about 2 to about 5 mm.

4. The intraocular lens of claim 1 wherein said optical body has a diameter of from about 4 to about 7 mm.

5. The intraocular lens of claim 4 having an overall diameter of from about 9 to about 11 mm, a central lens thickness of from about 3 to about 4 mm, a first component radius of curvature from about 9 to about 11 mm, and a second component radius of from about 6 to about 7.5 mm.

6. The intraocular lens of claim 1 wherein said first component has a radius of curvature of from about 8 to about 13 mm.

7. The intraocular lens of claim 1 wherein said second component has a radius of curvature of from about 5 to about 9 mm.

8. The intraocular lens of claim 1 wherein said at least one guiding structure is on the haptic body.

9. The intraocular lens of claim 1 wherein said at least one guiding structure is on the transition zone.

10. The intraocular lens of claim 1 wherein said lens is made from optically clear elastomeric materials.

11. The intraocular lens of claim 10 wherein the elastomeric material is selected from silicones, acrylic materials, hydrogels, and mixtures thereof.

* * * * *